(12) United States Patent
Mimoun et al.

(10) Patent No.: US 7,932,418 B2
(45) Date of Patent: Apr. 26, 2011

(54) PROCESS FOR THE PREPARATION OF β-γ ENE CARBONYL DERIVATIVES

(75) Inventors: Hubert Mimoun, Challex (FR); Serge Bonnaudet, Vouvray (FR)

(73) Assignee: Firmenich SA, Geneva (CH)

( * ) Notice: Subject to any disclaimer, the term of this patent is extended or adjusted under 35 U.S.C. 154(b) by 304 days.

(21) Appl. No.: 12/278,938

(22) PCT Filed: Feb. 1, 2007

(86) PCT No.: PCT/IB2007/050341
§ 371 (c)(1),
(2), (4) Date: Aug. 8, 2008

(87) PCT Pub. No.: WO2007/096791
PCT Pub. Date: Aug. 30, 2007

(65) Prior Publication Data
US 2010/0168462 A1    Jul. 1, 2010

(30) Foreign Application Priority Data
Feb. 23, 2006    (EP) .................................... 06110344

(51) Int. Cl.
C07C 69/52    (2006.01)
C07C 45/00    (2006.01)
(52) U.S. Cl. ................ 560/205; 568/400; 568/398
(58) Field of Classification Search ................ None
See application file for complete search history.

(56) References Cited

OTHER PUBLICATIONS

Corey, Journal of the American Chemical Society, The Mechanism of the Decarboxylation of alpha, beta—and beta, gamma—Unsaturated Malonic Acid Derivatives and the Course of Decarboxylative Condensation Reactions in Pyridine, 1952, 74, pp. 5807-5905.*
Corey, Journal of the American Chemical Society, The Decarboxylation of alpha, beta—Unsaturated Malonic Acid Derivatives via beta, gamma—Unsaturated Intermediates. II. The effect of alpha Substituents Upon Product Composition and Rate,1953, 75, pp. 1163-1167.*
International Search Report PCT/IB2007/050341 Dated Jun. 13, 2007.
R.V. Venkateswaran et al. *Decarbalkoxylation of Alkylidene Cyano Esters*, 1979, pp. 553-558, Tetrahedron Letters, No. 6, Pergamon Press Ltd.
K.H. Schulte-Elte et al., XP-002393151, *An Alternative Access to (±)—α—Irones and (±)—β—Irone via Acid-Mediated Cyclisation*, 1992, pp. 759-765, Helvetica Chimica Acta, vol. 75.
A.P. Krapcho, XP-000999104, *Synthetic Applications of Dealkoxycarbonylations of Malonate Esters, β-Keto Esters, α-Cyano Esters and Related Compounds in Dipolar Aprotic Media—Part 1*, 1982, pp. 805-822, Georg Thieme Verlag, Stuttgart, NY.
A.P. Krapcho, XP-000999105, *Synthetic Applications of Dealkoxycarbonylations of Malonate Esters, β-Keto Esters, α-Cyano Esters and Related Compounds in Dipolar Aprotic Media—Part 2*, 1982, pp. 893-914, Georg Thieme Verlag, Stuttgart, NY.
A.P. Krapcho, XP-002393152, *Synthetic Applications and Mechanism Studies of the Decarbalkoxylations of Geminal Diesters and Related Systems Effected in $Me_2SO$ by Water and/or by Water With Added Salts*, 1978, pp. 138-147, J. Org. Chemistry, vol. 43, No. 1, American Chemical Society.
A.H. Dickins, XP008067320, *The Chemistry of the Three-Carbon System, Part XX CycloPentylideneacetone and Cyclo-Pentylidenemethyl Ethyl Ketone*, 1929, pp. 572-580, Journal of the Chemical Society, London.
V. Ragoussis et al. *Palladium Catalyzed Reductive Decarboxylation of Allyl α-Alkenyl-β-Ketoesters. A New Synthesis of (E)-3-Alkenones*, 2006, pp. 683-687, Tetrahedron Letters 47, Elsevier Ltd. (2005).
I.D. Entwistle, *Use of 2-Nitrophenylpropionic Acid as a Protecting Group for Amino and Hydroxyl Functions to be Recovered by Hydrogen Transfer Reduction*, 1979, pp. 555-558, Tetrahedron Letters No. 6, Pargamon Press Ltd.

* cited by examiner

*Primary Examiner* — Paul A Zucker
(74) *Attorney, Agent, or Firm* — Winston & Strawn LLP

(57) ABSTRACT

The present invention relates to a preparation of β-γ ene carboxylic or ketone derivatives, which may also have particular requirement on the configuration of the carbon-carbon double bond. The method requires a thermal treatment of α-β unsaturated malonate or acetylacetonate derivatives in the presents of at least one carboxylic acid and at least one alkaline, alkaline-earth or lanthanide halide or carboxylates.

10 Claims, No Drawings

PROCESS FOR THE PREPARATION OF β-γ ENE CARBONYL DERIVATIVES

This application is a 371 filing of International Patent Application PCT/IB2007/050341 filed Feb. 1, 2007.

TECHNICAL FIELD

The present invention relates to the field of organic chemistry and, more particularly, to the preparation of β-γ ene carbonyl derivatives, which may also have particular requirement on the configuration of the carbon-carbon double bond.

PRIOR ART

The preparation of tri- or tetra substituted β-γ unsaturated ester or ketone derivatives by elimination on an acyl or carboxylic esters of an α-β unsaturated geminal dicarbonyl derivative is reported only in one reference (see V. Venkateswaran et al. in Tetrahedron Letters, 1979, 553.

In this article the authors report a reaction according to the following scheme:

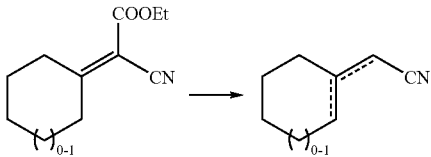

however, with this methodology the authors in two cases obtain a product wherein the major isomer is the α-β unsaturated derivative, to the contrary of the present invention, and in one case obtain a product wherein the major isomer is the β-γ unsaturated derivative, however with a poor selectivity.

In Helv.Chem-Acta, 1992, 759, by K. Schulte-Elte et al., there is disclosed a synthesis of 5,6-dimethylhept-4-en-2-one (with a β-γ/α-β ratio of about 13 and a β-γ E/Z ratio of about 2.2) by the demethoxycarbonylation of the corresponding alkylidene acetoacetate in the presence of DMSO, water and LiCl. Although the selectivities provided by this method are higher than the ones reported above, there is still an interested or need in improving them.

Indeed β-γ unsaturated ketones or esters can be useful intermediates in the preparation of important chemicals, there is still a need for a new or alternative process which allows their preparation with a good selectivity and therefore an increased yield. Furthermore, it is also important to prepare the desired β-γ unsaturated ketones or esters with a good selectivity in the configuration of the double bond, as it is sometime desired to obtain a product with a high content of the (E)-β-γ isomer.

DESCRIPTION OF THE INVENTION

In order to overcome the problems aforementioned, the present invention relates to processes for the preparation of a compound of formula (I)

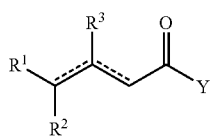

wherein the dotted lines indicate that the compound is in the form of a mixture of the corresponding β-γ or α-β unsaturated derivatives, the molar ratio β-γ/α-β being at least 3;

Y represent, independently of each other, a $OR^4$ or $R^4$ group, $R^4$ representing a $C_1$-$C_8$ hydrocarbon group, optionally comprising 1 to 3 heteroatoms selected from the group consisting of oxygen, sulfur and nitrogen;

$R^1$ represents a $C_1$-$C_{15}$ hydrocarbon group, optionally comprising 1 to 3 heteroatoms selected from the group consisting of oxygen, sulfur and nitrogen;

$R^2$ represents a $C_1$-$C_5$ hydrocarbon group, optionally comprising 1 to 3 heteroatoms selected from the group consisting of oxygen, sulfur and nitrogen;

$R^3$ represents a hydrogen atom or a $C_1$-$C_5$ hydrocarbon group; and optionally said $R_1$ and $R_2$, and/or $R_1$ and $R_3$, taken together may form a $C_4$-$C_{12}$ hydrocarbon group optionally comprising 1 to 3 heteroatoms selected from the group consisting of oxygen, sulfur and nitrogen;

said method comprising the step of reacting, at a temperature comprised between 100° C. and 230° C., a compound of formula

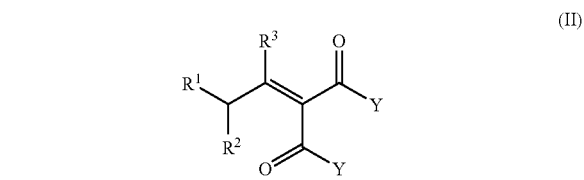

wherein Y, $R^1$, $R^2$ and $R^3$ are defined as in formula (I);

with at least one compound from the group i) and at least one compound from the group ii), said groups consisting respectively of:

i) the salts of formula $MX_2$, $M''X_3$ or $M'X$, wherein M is an alkali-earth cation and M' an alkali cation or $C_0$-$C_{12}$ ammonium cation and M" is a lanthanide cation, and X is a halide or an anion of an acid HX having a $pK_a$ comprised between 0 and 6;

ii) the carboxylic acids of formula $R^5COOH$, wherein $R^5$ represents a $C_1$-$C_{18}$ hydrocarbon group optionally comprising one or two oxygen atoms;

and optionally in the presence of a polar aprotic solvent having a boiling point of above 100° C.

According to an embodiment of the invention, the process concerns the preparation of a compound (I), starting from the corresponding compound (II), wherein:

the dotted lines indicate that the compound is in the form of a mixture of the corresponding β-γ or α-β unsaturated derivatives, the molar ratio β-γ/α-β being at least 3;

Y represent, independently of each other, a $OR^4$ or $R^4$ group, $R^4$ representing a $C_1$-$C_6$ alkyl group a phenyl group or a benzyl group;

$R^1$ represents a $C_2$-$C_{12}$ hydrocarbon atom, optionally comprising 1 to 3 functional hetero atoms selected from the group consisting of oxygen, sulfur and nitrogen;

$R^2$ represents a $C_1$-$C_3$ alkyl atom;

$R^3$ represents a hydrogen atom or a $C_1$-$C_3$ alkyl group; and optionally said $R_1$ and $R_2$, and/or $R_1$ and $R_3$, taken together may form a $C_5$-$C_{12}$ hydrocarbon atom optionally comprising 1 to 3 heteroatoms selected from the group consisting of oxygen, sulfur and nitrogen.

According to another embodiment of the invention, the compound of formula (I) is of formula

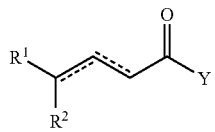

(III)

the dotted lines indicate that the compound is in the form of a mixture of the corresponding β-γ or α-β unsaturated derivatives, the molar ratio β-γ/α-β being at least 3;

Y represent, independently of each other, a $OR^4$ or $R^4$ group, $R^4$ representing a $C_1$-$C_6$ alkyl group or a $C_6$-$C_{10}$ phenyl or benzyl group optionally comprising 1 to 3 oxygen or nitrogen atoms;

$R^1$ represents a $C_2$-$C_{12}$ hydrocarbon atom, optionally comprising 1 to 3 functional oxygen or nitrogen atoms;

$R^2$ represents a $C_1$-$C_3$ alkyl group;

optionally said $R_1$ and $R_2$, taken together may form a $C_4$-$C_{11}$ hydrocarbon group optionally comprising 1 to 3 oxygen or nitrogen atoms.

Said compound of formula (III) are obtainable by the method according the invention by reacting, under the described condition, a compound of formula

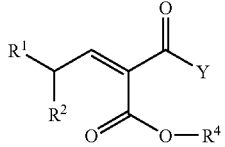

(IV)

wherein Y, $R^1$, $R^2$ and $R^4$ are defined as in formula (III).

According to any of the above-mentioned embodiments of the invention, the invention's process can be particularly useful when using compounds (II) wherein at least one Y is a $OR^4$ group, or even the two Y are $OR^4$ groups.

According to any of the above-mentioned embodiments of the invention, said hydrocarbon group is in the form of an alkyl, alkenyl, alkandienyl, aryl group or a mixture thereof, and said hydrocarbon group can be a linear, branched, cyclic group or a mixture thereof (e.g. comprises a linear alkyl, a (poly)cyclic alkenyl and an aryl moiety).

Furthermore, according to any of the above-mentioned embodiments of the invention, said compound (I) is obtained in the form of a mixture of the corresponding β-γ or α-β unsaturated derivatives wherein the molar ratio between β-γ derivative and the α-β derivative (i.e. β-γ/α-β) is at least 4 or even at least 6. Of particular interest are the processes wherein said ratio is above 8 or even above 15.

Simultaneously or alternatively to the above-mentioned selectivity of the β-γ/α-β ratio, according to any of the above-mentioned embodiments of the invention, said compound (I) is obtained in the form of a mixture of the corresponding β-γ or α-β unsaturated derivatives as mentioned above and wherein the molar ratio of the isomers E and Z of the β-γ unsaturated derivatives ((E)-β-γ)/((Z)-β-γ) is above 1, or even above 2. Furthermore, said ratio (E)/(Z) of the β-γ unsaturated derivative of formula (I) can be above 3 or even 4, and in some cases can be increased in order to be above 5.

In particular one may cite an embodiment wherein the compound of formula (I) is obtained in the form of a mixture of the corresponding β-γ or α-β unsaturated derivatives wherein β-γ/α-β is at least 5.5, or even 15, and the ratio of the isomers ((E)-β-γ)/((Z)-β-γ) is above 3.5.

Non-limiting examples of compound of formula (I) are compounds of formula

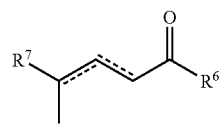

(V)

wherein $R^6$ represents a methyl or ethyl group or a OMe or OEt group; and $R^7$ represents
   a $C_{10-12}$ hydrocarbon group, such as a 2-(2,6,6-trimethyl-cyclohex-1-enyl)-ethyl group;
   a phenyl group optionally substituted with 1 or 2 $C_1$-$C_3$ alkoxy or amino groups; or
   a $C_3$-$C_6$ alkyl or alkenyl group.

Other examples of compound of formula (I) are

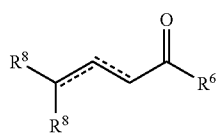

(VI)

wherein $R^6$ is as defined in formula (V) and the $R^8$ are taken together to form a $C_4$-$C_{11}$ hydrocarbon group, such as:
   a $CH_2(CH_2)_nCH_2$ n representing 2, 3, 4 or 9;
   an unsaturated $C_5$-$C_9$ hydrocarbon group.

According to alternative embodiments of the invention, the process is particularly useful for the compounds of formula (I) which are esters or alternatively ketones.

According to an embodiment of the formulae (V) or (VI), the invention's process can be particularly useful when using as starting material the corresponding compounds of formula (II) wherein at least one $R^6$ is a OMe or OEt group, or even the two $R^6$ are both OMe or OEt groups.

As mentioned above, the invention's process is run in the presence of at least one compound from the group i) and at least one compound from the group ii), said groups consisting respectively of:

i) the salts of formula $MX_2$, $M''X_3$ or $M'X$, wherein M is an alkali-earth cation and M' an alkali cation or $C_0$-$C_{12}$ ammonium cation and M'' is a lanthanide cation, and X is a halide or an anion of an acid HX having a $pK_a$ comprised between 0 and 6;

ii) the carboxylic acids of formula $R^5COOH$, wherein $R^5$ represents a $C_1$-$C_{18}$ hydrocarbon group optionally comprising one or two oxygen atoms;

and optionally in the presence of a polar aprotic solvent having a boiling point of above 100° C.

According to an embodiment of the invention, the reaction is carried out in the presence of at least one compound from the group i) and at least one compound from the group ii):

i) the salts of formula $MX_2$ or $M''X_3$, wherein M is an alkali-earth cation and M' an alkali cation or $C_0$-$C_{12}$ ammonium cation and M'' is a lanthanide cation, and X is a halide or an anion of an acid HX having a $pK_a$ comprised between 0 and 6; and ii) an acid $R^5COOH$, wherein $R^5$ represents a $C_1$-$C_{18}$ hydrocarbon group optionally comprising one or two oxygen atoms.

According to another embodiment of the invention, the compounds of group i) can be a magnesium, calcium, cerium, lithium, sodium or potassium salt of chloride, fluoride, iodine, or of a carboxylate of formula $R^9COO^-$, $R^9$ representing a $C_1$-$C_{18}$ hydrocarbon group optionally comprising one or two oxygen atoms.

In particular one may cite the chloride and the carboxylates salts.

Non-limiting examples of such salts are NaCl, NaF, NaI, $Mg(R^9COO)_2$, $R^9COONa$, $R^9COOK$, KF, $CeCl_3$, $Ce(R^9COO)_3$, $CaCl_2$ and $CaF_2$. This salt can be formed in situ, prior to its use, by reacting together the metal oxide or hydroxide with the required amount of the acid HX.

According to a particular embodiment of the invention, $R^9$ represents a $C_2$-$C_9$ alkyl, alkenyl, phenyl or benzyl group. In particular one may cite groups such as pent-2-yl, hept-3yl, propyl, isopropyl, isobutyl, tertbutyl, isopentyl, cyclohexyl, benzyl or $(Me)_2(CH_2)_3C(Me)=CH$.

In the case wherein the compound of formula (I) is an ester, the corresponding carboxylate can also be used.

According to an embodiment of the invention, the compounds of group ii) can be a carboxylic acid $R^9COOH$, wherein $R^9$ is as defined above.

According to an embodiment of the invention, the polar aprotic solvent can be a solvent having a boiling point of above 120° C. Furthermore it can be selected from the group consisting of a $C_2$-$C_6$ dialkyl sulfoxide, a $C_2$-$C_6$ dialkyl sulfone, a $C_3$-$C_7$ amide or lactam, a $C_3$-$C_8$ urea or pyrimidone derivative, $C_6$-$C_{12}$ phosphoramide or phosphino-amino derivative, a $C_3$-$C_8$ nitriles, a $C_4$-$C_8$ mono or diethylene glycol di-ether, and triethanolamine.

In particular one may cite the following: DMSO, NMP (N-methylpyrrolidone), DMF, HMPA, DMPU or diglyme.

The various compounds of the groups i) to iii) can be added to the reaction medium in a large range of concentrations. As non-limiting examples, one can cite as group i) concentration ranging from 0.5% to 200%, relative to the molar amount of the compound (II). Preferably, the group i) concentration will be comprised between 1% to 30%.

As non-limiting examples, one can cite as group ii) concentration ranging from 0.0% to 300%, relative to the molar amount of the compound (II). Preferably, the group ii) concentration will be comprised between 60% to 220%.

As non-limiting examples, one can cite as group iii) concentration ranging from 0.0% to 500%, relative to the weight of the compound (II). Preferably, the group iii) concentration will be comprised between 0.0% to 300%.

It goes without saying that the optimum concentrations of each compound of the various list will depend on the nature of the latter and of the compound (II).

The temperature at which the hydrogenation can be carried out is comprised between 100° C. and 230° C., more preferably in the range of between 120° C. and 190° C. Of course, a person skilled in the art is also able to select the preferred temperature as a function of the melting and boiling point of the starting and final products and of the desired speed of reaction.

The starting compounds (II) can be prepared according the standard method known by the person skilled in the art, and as also described in the examples. They may also be prepared in situ, also as described in the examples.

The invention will now be described in further detail by way of the following examples, wherein the temperatures are indicated in degrees centigrade and the abbreviations have the usual meaning in the art.

EXAMPLES

All the procedures described hereafter have been carried out under an inert atmosphere unless stated otherwise. All substrates and solvents were distilled from appropriate drying agents under Ar.

Example 1

A) General Procedure

The starting compound (II) (obtained according to the literature) (0.24 mol) (see Table 4) was heated at 160° C. for 10-9 h, in the presence of Mg(2-ethyl hexanate) (0.045 moles) and 2-ethyl hexanoic acid (0.24 mol). After cooling at 50° C., the mixture is washed with 10 g $H_2SO_4$ 20%, and distilled in vacuo to give the unsaturated esters. Table 4 gives the yields and the various isomers of compound (I).

TABLE 4

| Compound (II) | Compound (I) | Yield (%) | The ratio of the isomers |
|---|---|---|---|
| PhCHMeCH=C(COOMe)$_2$ | Methyl 4-phenyl-3-pentenoate | 80 | β-γ/α-β = 49<br>(E)-β-γ/(Z)-β-γ = 5.3/1 |
| Dimethyl [2-methyl-4-(2,6,6-trimethyl-1-cyclohexen-1-yl)butylidene]malonate | Methyl 4-methyl-6-(2,6,6-trimethyl-1-cyclohexen-1-yl)-3-hexenoate | 90 | β-γ/α-β = 49<br>(E)-β-γ/(Z)-β-γ = 5.1/1 |

B) General Procedure

Same experimental procedure as above, using as starting compound dimethyl [2-methyl-4-(2,6,6-trimethyl-1-cyclohexen-1-yl)butylidene]malonate and varying the catalyst. Results showed in Table 5.

TABLE 5

2-EH = 2-ethyl hexanoate

| Catalyst | Acid | Conversion | The ratio of the isomers |
|---|---|---|---|
| MgCl$_2$ | Propionic | 96 | β-γ/α-β = 28<br>(E)-β-γ/(Z)-β-γ = 4.7 |
| CeCl3 | Propionic | 100 | β-γ/α-β = 18<br>(E)-β-γ/(Z)-β-γ = 5.1 |
| LiCl | Propionic | 95 | β-γ/α-β = 8<br>(E)-β-γ/(Z)-β-γ = 4.8 |
| Mg(2-EH)$_2$ | 2-ethyl hexanoic | 98 | β-γ/α-β = 48<br>(E)-β-γ/(Z)-β-γ = 5.1 |
| Ca(2-EH)$_2$ | 2-ethyl hexanoic | 85 | β-γ/α-β = 17<br>(E)-β-γ/(Z)-β-γ = 8 |

The invention claimed is:

1. A process for the preparation of a compound of formula (I)

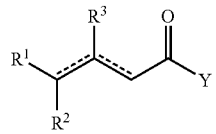

(I)

wherein:
the dotted lines indicate that the compound is in the form of a mixture of the corresponding β-γ or α-β unsaturated derivatives, the molar ratio β-γ/α-β being at least 3;

Y represents a $OR^4$ or $R^4$ group, $R^4$ representing a $C_1$-$C_8$ hydrocarbon group, optionally comprising 1 to 3 heteroatoms selected from the group consisting of oxygen, sulfur and nitrogen;

$R^1$ represents a $C_1$-$C_{15}$ hydrocarbon group, optionally comprising 1 to 3 heteroatoms selected from the group consisting of oxygen, sulfur and nitrogen;

$R^2$ represents a $C_1$-$C_5$ hydrocarbon group, optionally comprising 1 to 3 heteroatoms selected from the group consisting of oxygen, sulfur and nitrogen; and $R^3$ represents a hydrogen atom or a $C_1$-$C_5$ hydrocarbon group;

optionally wherein $R_1$ and $R_2$, or $R_1$ and $R_3$, taken together, form a $C_4$-$C_{12}$ hydrocarbon group optionally comprising 1 to 3 heteroatoms selected from the group consisting of oxygen, sulfur and nitrogen;

by a method which comprises:
reacting, at a temperature between 100° C. and 230° C., a compound of formula

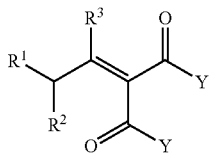

(II)

wherein Y, $R^1$, $R^2$ and $R^3$ are defined as in formula (I);

with at least one compound from the group i) and at least one compound from the group ii) to prepare the compound of formula I, wherein:

group i) is selected from the group consisting of salts of formula $MX_2$ and $M''X_3$, wherein M is an alkali-earth cation and M'' is a lanthanide cation, and X is a halide or an anion of an acid HX having a $pK_a$ value between 0 and 6; and group ii) is a carboxylic acid of formula $R^5COOH$, wherein $R^5$ represents a $C_1$-$C_{18}$ hydrocarbon group optionally comprising one or two oxygen atoms; and wherein the reaction is optionally conducted in the presence of a polar aprotic solvent having a boiling point of above 100° C.

2. A process according to claim 1, wherein the compound of formula (I) is of formula

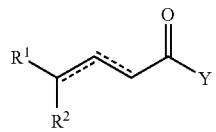

(III)

wherein:
the dotted lines indicate that the compound is in the form of a mixture of the corresponding β-γ or α-β unsaturated derivatives, the molar ratio β-γ/α-β being at least 3;

Y represents, independently of each other, a $OR^4$ or $R^4$ group, $R^4$ representing a $C_1$-$C_6$ alkyl group or a $C_6$-$C_{10}$ phenyl or benzyl group optionally comprising 1 to 3 oxygen or nitrogen atoms;

$R^1$ represents a $C_2$-$C_{12}$ hydrocarbon atom, optionally comprising 1 to 3 functional oxygen or nitrogen atoms; and $R^2$ represents a $C_1$-$C_3$ alkyl group;

with $R_1$ and $R_2$, taken together, optionally forming a $C_4$-$C_{11}$ hydrocarbon group optionally comprising 1 to 3 oxygen or nitrogen atoms.

3. A process according to claim 1, wherein compound (I) is obtained in the form of a mixture of the corresponding β-γ or α-β unsaturated derivatives, wherein:
β-γ/α-β is at least 6; or
isomers E and Z of the β-γ unsaturated derivatives, ((E)-β-γ)/((Z)-β-γ), are present in a molar ratio of above 3.

4. A process according to claim 1, wherein the compound of formula (I) is a compound of formula V

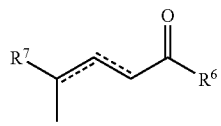

(V)

wherein $R^6$ represents a methyl or ethyl group or a OMe or OEt group; and $R^7$ represents:
a $C_{10-12}$ hydrocarbon group;
a phenyl group optionally substituted with 1 or 2 $C_1$-$C_3$ alkoxy or amino groups; or
a $C_3$-$C_6$ alkyl or alkenyl group.

5. A process according to claim 1, wherein the compound of formula (II) is reacted in the presence of at least one compound from group iii) and at least one compound from the group iv), wherein:

group iii) is selected from the group consisting of salts of formula $MX_2$, $M''X_3$ and M'X, wherein M is an alkali-earth cation and M' an alkali cation or $C_0$-$C_{12}$ ammonium cation and M'' is a lanthanide cation, and X is a halide or an anion of an acid HX having a $pK_a$ value between 0 and 6, in particular a $MX_2$ or $M''X_3$ salt; and group iv) is an acid $R^5COOH$, wherein $R^5$ represents a $C_1$-$C_{18}$ hydrocarbon group optionally including one or two oxygen atoms.

6. A process according to claim 5, wherein the compound of group iii) is a salt of formula $MX_2$ or $M''X_3$.

7. A process according to claim 5, wherein the compound of group iii) is a magnesium, calcium, cerium, lithium, sodium or potassium salt of chlorine, fluorine, iodine, or of a carboxylate of formula $R^9COO^-$, $R^9$ representing a $C_1$-$C_{18}$ hydrocarbon group optionally including one or two oxygen atoms.

8. A process according to claim 7, wherein the group iii) salt is NaCl, NaF, NaI, $Mg(R^9COO)_2$, $R^9COONa$, $R^9COOK$, KF, $CeCl_3$, $Ce(R^9COO)_3$, $CaCl_2$ or $CaF_2$, $R^9$ being defined as in claim 7.

9. A process according to claim 1, wherein the compound of group iv) is a carboxylic acid $R^9COOH$, wherein $R^9$ is a $C_2$-$C_9$ alkyl, alkenyl, phenyl or benzyl group.

10. A process according to claim 9, wherein $R^9$ represents a pent-2-yl, hept-3yl, propyl, isopropyl, isobutyl, tertbutyl, isopentyl, cyclohexyl, benzyl or $(Me)_2(CH_2)_3C(Me)=CH$ group.

* * * * *